United States Patent [19]

Laerum

[11] Patent Number: 4,499,081
[45] Date of Patent: Feb. 12, 1985

[54] PEPTIDE COMPOUNDS
[75] Inventor: Ole D. Laerum, Bergen, Norway
[73] Assignee: Nyegaard & Co A/S, Oslo, Norway
[21] Appl. No.: 555,840
[22] Filed: Nov. 28, 1983

[30] Foreign Application Priority Data

Nov. 26, 1982 [GB] United Kingdom ............... 8233837

[51] Int. Cl.$^3$ .................. A61K 37/00; C07C 103/52
[52] U.S. Cl. .............................. 514/17; 260/112.5 R; 514/18
[58] Field of Search ................. 260/112.5 R; 424/177

[56] References Cited

U.S. PATENT DOCUMENTS

| | | | |
|---|---|---|---|
| 3,792,032 | 2/1974 | Bernardi et al. | 260/112.5 R |
| 3,928,306 | 12/1975 | Uchiyama et al. | 260/112.5 R |
| 4,235,772 | 11/1980 | Lundin et al. | 260/112.5 R |
| 4,411,890 | 10/1983 | Momany | 260/112.5 R |
| 4,412,988 | 11/1983 | Gasc et al. | 260/112.5 R |

FOREIGN PATENT DOCUMENTS 2465486  9/1979  France .

OTHER PUBLICATIONS

Notizen, vol. 37, pp. 1297–1300 (1982).
Chem. Abstr., vol 99, (1983) 1022q.
P. Foa, L. Lombardi, A. Ciani, F. Chillemi, A. T. Maiolo, E. E. Polli and B. M. Cesana, "A Synthetic Pentapeptide Inhibiting Normal and Leukaemic Myelopoiesis In Vitro", IRCS Med. Sci.: Libr. Compend., 1983, 11 (3), pp. 272–273.

Primary Examiner—Delbert R. Phillips
Attorney, Agent, or Firm—Bacon & Thomas

[57] ABSTRACT

The invention provides compounds of the general formula:

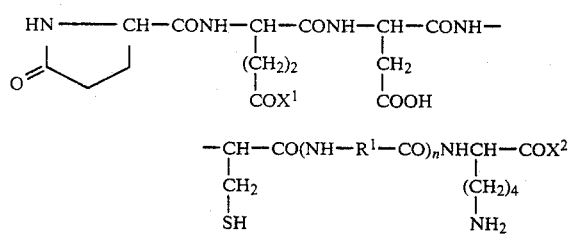

(in which $R^1$ is the residue of glycine or D-alanine, and all other amino-acid residues are in the L-form, $X^1$ and $X^2$, which may be the same or different, are OH or $NH_2$ and n is 0 or 1) and their physiologically acceptable salts.

The compounds of the invention are capable of inhibiting the myelopoietic system of humans and animals, thereby protecting said system against attack by cytotoxic drugs.

7 Claims, No Drawings

PEPTIDE COMPOUNDS

The present invention relates to novel peptides having an inhibitory effect on hemopoiesis and to a process for their preparation.

Many of the most effective cancer treatment regimens utilise cytotoxic drugs which attack the cancer cells during mitosis and in the S-phase. Normal tissue cells undergoing cell division are usually affected simultaneously but the majority of such cells are quiescent and so not vulnerable to attack. However, it has been observed that such cytotoxic drugs not only attack the poliferating tissue cells but tend to trigger a large proportion of normally quiescent hemopoietic stem cells in the bone marrow into cell cycle, thus rendering them susceptible to attack.

The bone marrow cells derive from pluripotent stem cells which mature to form a complex population of morphologically distinct cells, namely megakaryocytes, erythrocytes, granulocytes and lymphocytes. Only about 10% of the pluripotent stem cells are in cell division at any time. In an initial phase of maturation each of the proliferating stem cells becomes "committed" to a particular morphologically distinct form eventually leading to one of the above four mature cells types. As the cells proliferate they gradually lose the power of further proliferation and the mature cells, for example, erythrocytes or granulocytes, can no longer divide. Consequently, since the mature cells are continually dying, it is essential that the proliferative ability of the less mature cells, and in particular the pluripotent stem cells, is maintained.

We have now found certain peptides which are capable of selectively preventing quiescent stem cells from being triggered into cycle. The peptides are believed to be analogues of a naturally occurring granulopoiesis inhibition factor which has been found in minute quantities in bone marrow extracts.

According to the present invention, therefore, we provide compounds of the general formula:

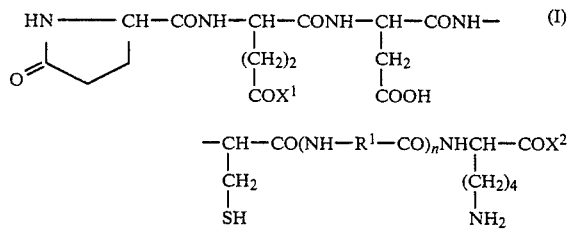

(in which $R^1$ is the residue of glycine or D-alanine, and all other amino-acid residues are in the L-form, $X^1$ and $X^2$ which may be the same or different, are OH or $NH_2$ and n is 0 or 1) and their physiologically acceptable salts.

Physiologically acceptable salts of the peptides of the invention include acid addition salts such as the hydrochlorides, hydrobromides, sulphates, etc. as well as salts with bases such as alkali metal salts, e.g. sodium or potassium salts, alkaline earth metal salts, e.g. calcium salts or amine salts.

The amino acid residue at the second position from the N-terminal end appears to be critical, since the peptide pyroGlu-Asp-Asp-Cys-LysOH which had been postulated as the naturally occurring granulopoiesis inhibition factor proved to be inactive. Due to the minute amounts of the natural granulopoiesis factor available, the structure of the natural substance has not been determined. It has never been obtained in crystalline or completely pure form and it is not known whether this could be achieved using material from natural sources only. In contrast, the peptides of the invention can be obtained in crystalline form suitable for pharmaceutical use and in relatively large quantities, free from contaminating peptides and proteins of natural origin.

The preferred compounds of the invention are
(1) L-pyroGlutamyl-L-glutamyl-L-aspartyl-L-cysteinyl-L-lysine;
(2) L-pyroGlutamyl-L-glutamyl-L-aspartyl-L-cysteinylglycyl-L-lysine;
(3) L-pyroGlutamyl-L-glutaminyl-L-aspartyl-L-cysteinyl-L-lysine;
(4) L-pyroGlutamyl-L-glutamyl-L-aspartyl-L-cysteinyl-D-alanyl-L-lysine; and
(5) L-pyroGlutamyl-L-glutamyl-L-aspartyl-L-cysteinyl-L-lysine amide.

The compounds of the above formula tend to exhibit a complex pattern of activity which is apparently dose-dependent. In particular, Compound (1) when injected into mice at a relatively low dose level shows a selective inhibition of the myelopoietic system, namely inhibition of the morphologically recognisable cells and committed stem cells, whereas other cell lineages deriving from the pluripotent stem cells are not affected. At a concentration of $10^{-7}M$ in the extracellular fluid there is a marked decrease in peripheral granulocytes which is greatest in the mature cells. After one injection at $10^{-5}M$, the main effect appears to be on committed stem cells. At higher doses, e.g. injections at $10^{-5}M$ for six successive days, there is still a strong reduction in the population of committed stem cells but also the pluripotent stem cells and the production of erythrocytes are reduced. At $10^{-5}M$ for three weeks, strong stimulation of the whole hemopoietic system is observed, including production of lymphocytes. Similar results are exhibited by Compounds (2)–(5), although at slightly different levels of potency.

It should be noted that there is no inhibitory effect on the cells of other tissues and in particular on tumour cells related to non-myelopoietic tissues. They thus protect the myelopoietic system selectively. However, the peptides exert a protective effect on cancer cells related to the myelopoietic system, for example, myeloleukemic cells, and cannot be used selectively in treatment of such cancers.

The peptides are without significant toxicity. Furthermore, all the hematological effects observed were reversible and no macrocopic changes were observed in the other organs of the animals injected with the peptides.

As indicated above, inhibition of hemopoiesis and, in particular, granulopoiesis tends to prevent quiescent cells from entering into cell division and so becoming susceptible to attack by cytotoxic anti-cancer drugs, for example cytosine arabinoside.

We have noted that after treatment with a peptide of the invention such as Compound (1), the inhibitory effect on the myelopoietic cells is not merely reversible but, in fact, production of such cells is temporarily abnormally increased, so that the normal cell population is very rapidly restored and, indeed, overshoots temporarily.

In addition to the above protective function in therapy using cytotoxic drugs, the peptides according to the invention may also be used to arrest proliferation of cancer cells related to the myelopoietic system, for example in the treatment of myeloleukaemia. The peptides may be used in any clinical situation where it is desirable to alter hemopoiesis. In some cases, the peptides according to the invention may also be used at relatively high doses to stimulate the myelopoietic system where this is insufficiently active.

Since the peptides have been found to exert a certain influence on related non-myeloid cells such as lymphopoiesis, they may also be used for selective modification of cell proliferation in other organs.

In general, in order to exert a protective effect against cytotoxic drugs, the peptides of the invention may be administered to human patients by injection in the dose range 1–10 mg, for example 4–5 mg, per 70 kg body weight per day. If administered by infusion or similar techniques, the dose may be in the range 30–300 mg per 70 kg body weight, for example about 100 mg, over six days. In principle it is desirable to produce a concentration of the peptide of about $10^{-9}M$ to $10^{-4}M$ in the extracellular fluid of the patient.

In general, combined therapy with cytotoxic drugs such as cytosine arabinoside requires careful timing to ensure that the myelopoietic system is protected while the cytotoxic drug is still present.

According to a still further feature of the present invention there are provided pharmaceutical compositions comprising as active ingredient at least one compound of formula (I) as hereinbefore defined or a physiologically compatible salt thereof, in association with a pharmaceutical carrier or excipient. The compositions according to the invention may be presented, for example, in a form suitable for oral, nasal, parenteral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 1–10 mg, for example 4–5 mg of the peptide of formula (I).

According to a still further feature of the present invention there is provided a method of inhibition of hemopoiesis which comprises administering an effective amount of a pharmaceutical composition as hereinabove defined to a subject.

A further major use of the new peptides, however, is in the production of material for immunological assay techniques. The peptide may then be covalently attached to a suitable high molecular carrier such as albumin, polysine or polyproline in order to be injected into antibody-producing animals (e.g. rabbits, guinea pigs or goats). High specificity antisera are obtained by use of well known absorption techniques, using the high molecular carrier. By introducing radioactivity ($^3H$, $^{14}C$, $^{18}O$, $^{15}N$) into the peptide molecule, a radioimmuno assay can readily be designed and used for determining the peptide in the different biological fluids such as serum (plasma), urine and cerebrospinal fluid.

The peptides of the invention may be synthesised in any convenient way. In general, the reactive groups present (amino, thiol and/or carboxyl) will be protected during the overall synthesis and the final stage will thus be the deprotection of a protected derivative of formula (I). Normally, all —COOH groups, all —NH₂ groups, the —NH group of the pyroglutamyl residue and the —SH group of the cysteinyl residue will be protected.

The protected compound may thus have the formula

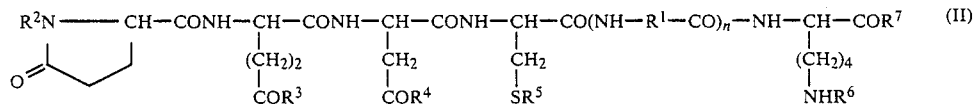

agents for obtaining sustained release, such as carboxypolymethylene, carboxymethyl cellulose, cellulose acetate phthalate, or polyvinylacetate.

wherein $R^2$ and $R^6$ are amine protecting groups or hydrogen atoms, $R^3$, $R^4$ and $R^7$ are $NH_2$, protected amino or carboxyl protecting groups or OH and $R^5$ is a thiol protecting group.

A wide choice of protecting groups for aminoacids are known and are exemplified in Schr,öder, E., and L,übke, K., The Peptides, Vols. 1 and 2, Academic Press, New York and London, 1965 and 1966; Pettit, G. R., Synthetic Peptides, Vols. 1–4, Van Nostrand, Reinhold, New York 1970, 1971, 1975 and 1976, Houben-Weyl, Methoden der Organischen Chemie, Synthese von Peptiden, Band 15, Georg Thiene Verlag, Stuttgart 1974; and Amino Acids, Peptides and Proteins, Vol. 4-8, The Chemical Society, London 1972, 1974, 1975 and 1976.

Thus, for example amine protecting groups which may be employed include the carbobenzoxy (hereinafter also designated Z) trityl, t-butoxycarbonyl (hereinafter also designated Boc) and acyl groups such as, for example, an acetyl group or a formyl group.

Carboxyl protecting groups which may, for example be employed include readily cleaved ester groups such as benzyl (hereinafter also designated Bz), p-nitrobenzyl or t-butyl groups.

Thiol protecting groups include p-methoxybenzyl and sulphoethyl groups.

It will be appreciated that a wide range of other such groups exists as, for example, detailed in the above-mentioned literature references, and the use of all such groups in the hereinbefore described processes fall within the scope of the present invention.

Carboxyl protecting groups may be introduced by conventional methods e.g. by reaction with a suitable esterifying reagent, for example an alcohol such as benzyl or p-nitrobenzyl alcohol in the presence of acid, e.g. p-toluenesulphonic acid.

Amine-protecting groups may be introduced by conventional methods e.g. by reaction with suitable acid halides such as carbobenzoxy chloride or pivaloyl chloride, or acid anhydrides such as acetic anhydride.

Thiol protecting groups may be introduced by reaction with suitable S-etherifying agents such as p-methoxybenzyl chloride or sulphoethyl bromide.

A wide range of procedures exists for removing amine- and carboxyl-protecting groups. Thus, for example an amine-protecting group may be removed by acidolysis, hydrogenolysis, treatment with dilute ammonium hydroxide, treatment with sodium, treatment with sodium amide, treatment with hydrazine, or enzymatic hydrolysis with, for example, leucineamino-peptidase. Methods which are of interest also include treatment with anhydrous hydrogen bromide for example in glacial acetic acid, treatment with trifluoroacetic acid, treatment with liquid hydrogen fluoride and catalytic hydrogenation.

Thus carbobenzoxy and t-butoxy carbonyl groups may be removed, for example, using anhydrous hydrogen bromide conveniently in the presence of glacial acetic acid or using trifluoroacetic acid. Acyl groups may for example be removed by conventional hydrolysis with acid or by enzymatic hydrolysis as described above.

The removal of carboxyl protecting groups may, for example, be effected by saponification, acidolysis, hydrogenolysis or enzymatic hydrolysis. Thus, for example, saponification may be effected with an alkali metal hydroxide conveniently in the presence of water, an alcohol and/or acetone. Acidolysis may, for example, be effected by the use of anhydrous hydrogen bromide or trifluoroacetic acid and hydrogenolysis may, for example be effected by catalytic hydrogenation e.g. by the use of palladium on carbon, conveniently 10% palladium on charcoal. Enzymatic hydrolysis may, for example, be effected by the use of leucineaminopeptidase. Thus, for example, benzyl and p-nitrobenzyl groups may be removed by hydrogenolysis and t-butyl groups may, for example, be removed by acid hydrolysis.

Amine-, hydroxyl- and carboxyl-protecting groups may, for example, be removed simultaneously by acidolysis, alkaline hydrolysis, hydrogenolysis, treatment with sodium or sodium amide or by enzymatic hydrolysis. Such methods include treatment with hydrogen bromide, conveniently in the presence of glacial acetic acid, and treatment with alcohol conveniently containing dissolved dry hydrogen chloride.

Thiol protecting groups such as p-methoxybenzyl groups may be removed using hydrogen fluoride at a low temperature, e.g. 0° C., advantageously in the presence of a scavenger such as mercaptoethanol, cysteine or methionine. This method is capable of removing amino-, carboxyl- and thiol-protecting groups simultaneously.

One method of selective deprotection is, for example, catalytic hydrogenation, conveniently using palladium on, for example, carbon, as the catalyst and conveniently in the presence of a solvent e.g. water, methanol, dioxan, acetic acid or t-butanol. This method removes, for example, the carbobenzoxy group, but leaves the t-butoxy-carbonyl or an acyl group intact.

In general, the protected derivatives of the compounds of formula (I) can be prepared by way of the techniques appropriate for peptide synthesis. One can start at the C-terminal by reaction of a suitably protected derivative of lysine with a suitably protected derivative of cysteine or, when n=1, the compound $NH_2R^1$ COOH. The lysine derivative will have a free α-amino group while the other reactant will have either a free or activated carboxyl group and a protected amino group. After coupling, the intermediate may be purified, for example by chromatography, and then selectively N-deprotected to permit addition of a further amino acid residue. This procedure is continued until the required amino acid sequence is completed. N-deprotection will normally be effected by mild acidolysis; the excess acid is normally neutralised before the next coupling step, e.g. using a base such as triethylamine.

Alternatively, it is possible to start at the N-terminal and react a suitably protected glutamic or pyroglutamic acid derivative, preferably having an activated carboxyl group, with a suitably protected derivative of glutamic acid or glutamine. After coupling, the product may be purified e.g. by chromatography, and the terminal α-carboxyl group deprotected and, if desired, activated, prior to the next coupling step. This sequence of steps is repeated until the desired peptide is complete.

Carboxylic acid activating substituents which may, for example, be employed include mixed anhydrides, azides or activated esters such as for example the p-nitrophenyl ester, 2,4,5-trichlorophenyl ester, N-hydroxybenzotriazole ester, or N-hydroxysuccinimidyl ester.

In general it is convenient to effect the coupling reactions at low temperatures, for example, −20° C. up to ambient temperature, conveniently in a suitable solvent system, for example, tetrahydrofuran, dioxan, dimethylformamide, methylene chloride or a mixture of these solvents.

The coupling of free amino and carboxyl groups may, for example, be effected using dicyclohexylcarbodiimide (DCC). Another coupling agent which may, for example, be employed is N-ethoxycarbonyl-2-ethoxy-1,2-dihydroquinoline.

It may be more convenient to carry out the synthesis on a solid phase resin support. Chloromethylated polystyrene (cross-linked with 1% divinyl benzene) is one useful type of support; in this case the synthesis will start at the C-terminal by coupling N-protected lysine to the support. Where $X^2$ is to be $NH_2$, it is preferable to use a resin support carrying benzhydrylamine groups; these are initially coupled to the lysine carboxyl group and final cleavage, e.g. with HF, yields the desired amide.

The following Examples are given by way of illustration only.

Solvents were redistilled from commercial material and stored in the following way: Dimethylformamide (DMF) over molecular sieve 4 A, dichloromethane (DCM) over $CaCl_2$, triethylamine (TEA) over Na/Pb alloy (Baker) and trifluoroacetic acid (TFA) over molecular sieve 4 A.

EXAMPLE 1

L-PYROGLUTAMYL-L-GLUTAMYL-L-ASPARTYL-L-CYSTEINYL-L-LYSINE: Compound (1)

(a) t-Boc-(S-p-METHOXYBENZYL)-L-CYSTEINYL-(ε-BENZYLOXYCARBONYL)-L-LYSINE BENZYLESTER (I)

ε-Benzyloxycarbonyl-lysine benzylester hydrochloride (406 mg) is dissolved in 3 ml of DMF and TEA is added until free TEA can be detected in the vapor phase with a wetted piece of pH indicator paper. To this solution t-Boc-(S-p-methoxybenzyl)-L-cysteine N-hydroxysuccinimide ester (491 mg) dissolved in 3 ml DMF is added. At appropriate time intervals portions of TEA are added to maintain the slight alkalinity of the solution. The mixture is left overnight at room temperature and after checking for a negative ninhydrin reaction is directly applied to a 2.5×75 cm column of Sephadex LH-20, equilibrated with DMF and calibrated with standard reactants (eg in the example given t-Boc-(γ-benzyl)-L-glutamic acid-p-nitrophenylester and p-nitro-phenol). Column flow is maintained by gravity flow and the effluent is monitored at 280 nm before collection in fractions of approximately 10 ml. The product may be identified by t.l.c. of each fraction, the respective fractions being pooled and evaporated in vacuo; yield: 700 mg (100%) of an oily product, homogeneous in t.l.c. (chloroform/acetone (9/1)), $R_f=0.64$.

(b) t-Boc-(β-BENZYL)-L-ASPARTYL-(S-p-METHOXYBENZYL)-L-CYSTEINYL-(ε-BENZYLOXYCARBONYL)-L-LYSINE BENZYLESTER (II)

700 mg of the blocked and protected dipeptide (I) are dissolved in 25 ml of anhydrous DCM and 25 ml of anhydrous TFA are added. After 30 min acid and solvent are removed in vacuo. The residue is dissolved in DCM and again evaporated. To a solution of the residue in DMF (3 ml) which is made slightly alkaline with TEA a solution of t-Boc-(β-benzyl)-L-aspartic acid p-nitrophenylester (488 mg) in 3 ml DMF is added. Alkalinity should be frequently checked and maintained by additions of small amounts of TEA. After the ninhydrin reaction had become negative (after about 2 hrs) the reaction mixture is applied to a Sephadex LH-20 column (2.5×75 cm) and purified as described above. Yield after evaporation in vacuo; ~900 mg (100%) of a crystalline product, homogeneous on t.l.c. (chloroform/acetone (9/1)), $R_f=0.70$.

(c) t-Boc-(γ-BENZYL)-L-GLUTAMYL-(β-BENZYL)-L-ASPARTYL-(S-p-METHOXYBENZYL)-L-CYSTEINYL-(ε-BENZYLOXYCARBONYL)-L-LYSINE BENZYLESTER (III)

900 mg of the blocked tripeptide derivative II are deblocked with TFA as described above, dissolved in 3 ml of DMF and made slightly alkaline with TEA. To this solution 504 mg of t-Boc-(γ-benzyl)-L-glutamic acid p-nitrophenylester (in 3 ml of DMF) are added. After about 2.5 hrs the ninhydrin reaction has become negative and the mixture is applied to a Sephadex LH-20 column for purification as described above. The separation of the components in this reaction mixture and its monitoring by t.l.c. may be carried out as above. The appropriate fractions (9–15 in this case) are pooled, evaporated and dried. Yield: ~1140 mg (100%) of a pale yellowish oil, homogeneous on t.l.c. (chloroform/acetone (9/1)), $R_f=0.53$.

(d) BENZYLOXYCARBONYL-L-PYROGLUTAMYL-(γ-BENZYL)-L-GLUTAMYL-(β-BENZYL)-L-ASPARTYL-(S-p-METHOXYBENZYL)-L-CYSTEINYL-(ε-BENZYL-OXYCARBONYL)-L-LYSINE BENZYLESTER (IV)

1140 mg of the tetrapeptide derivative III are deblocked with TFA in DCM as described for I and dissolved in 3 ml DMF. The solution is made slightly alkaline with TEA and 423 mg of benzyloxycarbonyl-L-pyroglutamic acid p-nitrophenylester are added as a solution in 3 ml DMF. Alkalinity of the reaction mixture should be repeatedly checked and if necessary restored by addition of TEA. After about 3 hrs the ninhydrin test becomes negative and the pentapeptide derivative IV may be purified as described above. Yield ~1230 mg (96%), pale yellowish oil, homogeneous on t.l.c. (chloroform/acetone (9/1)), $R_f=0.44$ (with tailing).

(e) L-PYROGLUTAMYL-L-GLUTAMYL-L-ASPARTYL-L-CYSTEINYL-L-LYSINE 50 mg of the protected pentapeptide derivative IV are dissolved in 50 ml liquid hydrogen fluoride at 0° C. with the addition of 500 mg methionine as a scavenger and left for 1 hour. The hydrogen fluoride is then evaporated to dryness in vacuo at 0° C. and the residue stirred with ethyl acetate. The ethyl acetate washing is decanted and discarded. The remaining material is dissolved in dilute acetic acid and lyophilised.

The lyophilised material (2 mg) may be purified by reversed phase HPLC using a C18-column 10 mm×10 cm at a flow rate of 2.8 ml per minute using gradient elution with solution A: 0.1% aqueous trifluoroacetic acid and solution B: 0.1% trifluoroacetic acid in acetonitrile; 0.10% of solution B being added over 30 minutes. Detection is effected using ultraviolet absorption at 214 nm or pyridine disulphide reagent (for SH-groups).

The same procedure may be used to prepare the abovementioned Compounds (2) to (5). The syntheses are set out below in schematic form and the characteristics of the products are given in the Table. The following abbreviations are used:

Boc=t-butoxycarbonyl
Bz=benzyl
Z=benzyloxycarbonyl (carbobenzoxy)
pMB=p-methoxybenzyl
Su=N-hydroxysuccinimyl
pNP=p-nitrophenyl Compound 1
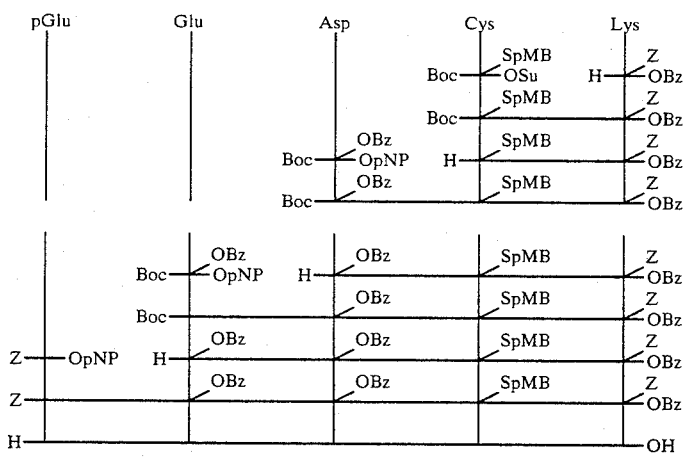
Compound 2
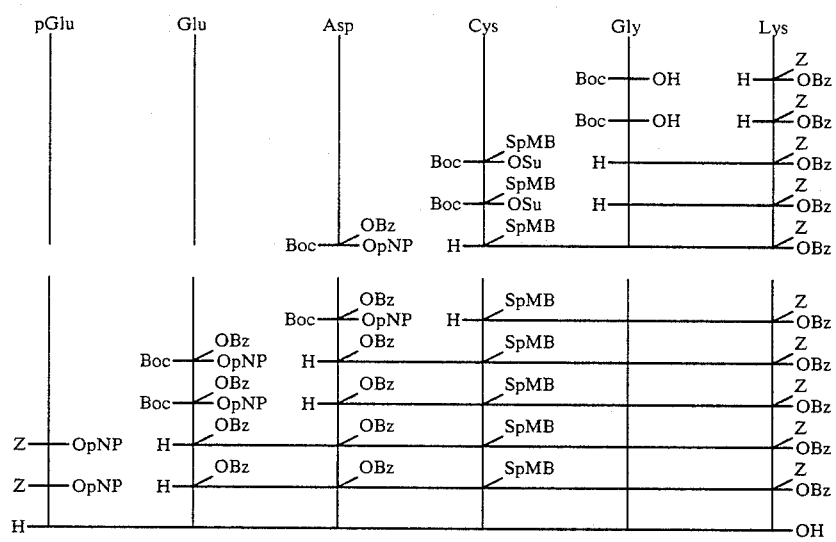
Compound 3
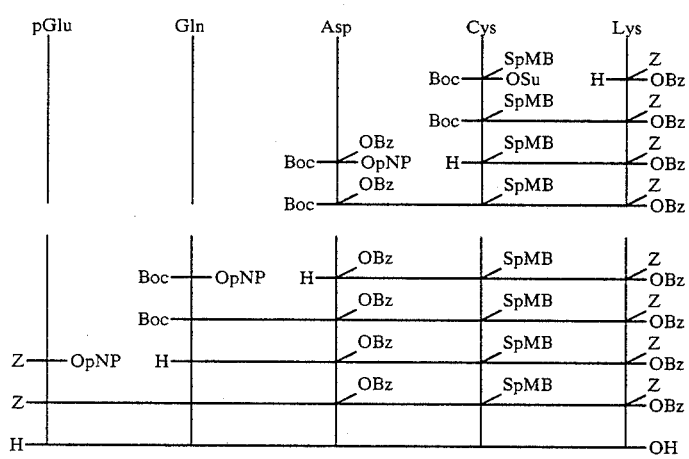
Compound 4

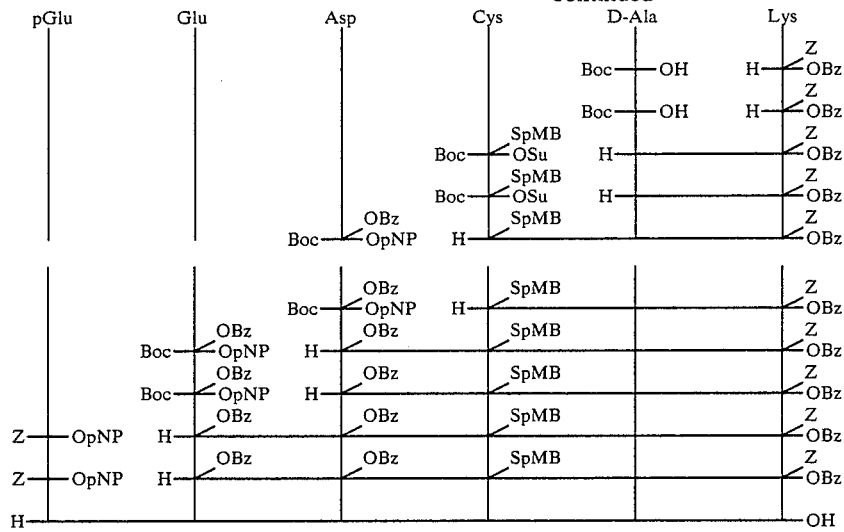

Compound 5

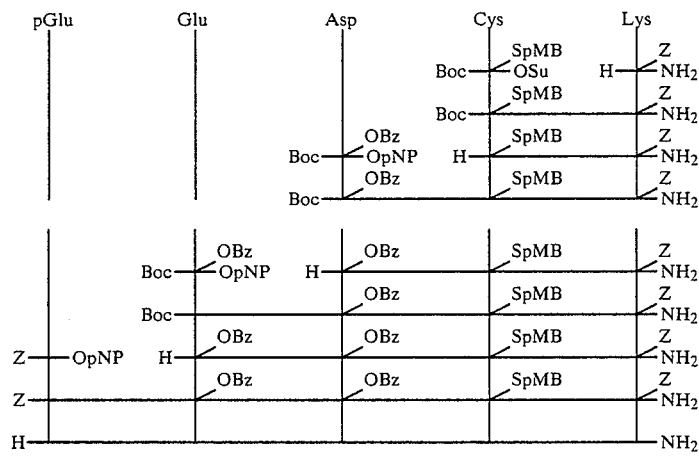

| | | Compound (1) | Compound (2) | Compound (3) | Compound (4) | Compound (5) |
|---|---|---|---|---|---|---|
| (I) | TLC Silica gel Solvent | | | | | |
| (a) | nBuOH:EtOAC:Formicacid:Ag 1:1:1:1 | $R_f = 0.21$ | $R_f = 0.19$ | $R_f = 0.15$ | $R_f = 0.22$ | $R_f = 0.15$ |
| (b) | Pyridine:EtOAC:HOAc:Ag 5:5:1:3 | $R_f = 0.07$ | $R_f = 0.08$ | $R_f = 0.08$ | $R_f = 0.08$ | $R_f = 0.14$ |
| (II) | Amino acid analysis | | | | | |
| | Ala | — | — | — | 1.01 | — |
| | Asp | 1.00 | 1.00 | 1.00 | 1.00 | 1.00 |
| | Glu | 1.98 | 1.91 | 1.87 | 1.94 | 1.87 |
| | Gly | — | 0.98 | — | — | — |
| | Cys | 0.98 | 0.90 | 0.90 | 0.89 | 0.88 |
| | Lys | 1.04 | 1.09 | 0.98 | 1.09 | 1.00 |
| (III) | HPLC $C_{18}$ 5 μm 125 × 4 mm DCf:214 mm Flow 1 ml/m A: 5 mM phosphoric acid B: 80% Flow: mM phosphoric acid/20% $CH_3CN$ | RT 15.7 | RT 16.7 | RT 8.8 | RT 18.3 | RT 10.0 |

| Time | % B |
|---|---|
| 0 | 0 |
| 18 | 20 |
| 30 | 100 |

I claim:

1. A compound of the formula:

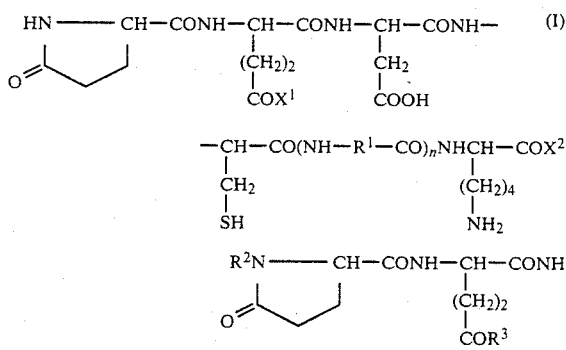

(in which $R^1$ is the residue of glycine or D-alanine, and all other amino-acid residues are in the L-form, $X^1$ and $X^2$, which may be the same or different, are OH or $NH_2$ and n is 0 or 1) and their physiologically acceptable salts.

2. A compound which is L-pyroGlutamyl-L-glutaminyl-L-aspartyl-L-cysteinyl-L-lysine;

L-pyroGlutamyl-L-glutamyl-L-aspartyl-L-cysteinyl-glycyl-L-lysine;

L-pyroGlutamyl-L-glutamyl-L-aspartyl-L-cysteinyl-L-lysine;

L-pyroGlutamyl-L-glutamyl-L-aspartyl-L-cysteinyl-D-alanyl-L-lysine; or

L-pyroGlutamyl-L-glutamyl-L-aspartyl-L-cysteinyl-L-lysine amide.

3. A compound as claimed in claim 1 in crystalline form.

4. A compound as claimed in claim 2 in crystalline form.

5. A compound of the formula II:

$$R^2N-CH-CONH-CH-CONH-CH-CONH-CH-CO(NH-R^1-CO)_n-NH-CH-COR^7 \quad (II)$$

with substituents: $O=$, $(CH_2)_2$, $COR^3$, $CH_2$, $COR^4$, $CH_2$, $SR^5$, $(CH_2)_4$, $NHR^6$ wherein $R^1$ is the residue of glycine or D-alanine, and all other amino acid residues are in the L-form, $R^2$ and $R^6$ are amine protecting groups or hydrogen atoms, $R^3$, $R^4$ and $R^7$ are $NH_2$, protected amino or carboxyl protecting groups or OH, $R^5$ is a thiol protecting group, and n is zero or one, and the physiologically acceptable salts thereof.

6. A pharmaceutical composition comprising a compound as claimed in claim 1 in conjunction with a pharmaceutical carrier or excipient.

7. A method of inhibiting the myelopoietic system of a human or animal subject in which an effective dose of a compound as claimed in claim 1 is administered to said subject.

* * * * *